(12) United States Patent
Sartor (10) Patent No.: US 7,828,794 B2
(45) Date of Patent: Nov. 9, 2010

(54) HANDHELD ELECTROSURGICAL APPARATUS FOR CONTROLLING OPERATING ROOM EQUIPMENT

(75) Inventor: Joe Don Sartor, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 597 days.

(21) Appl. No.: 11/211,293

(22) Filed: Aug. 25, 2005

(65) Prior Publication Data

US 2007/0049926 A1  Mar. 1, 2007

(51) Int. Cl.
*A61B 18/04* (2006.01)
(52) U.S. Cl. .......................... 606/34; 606/42
(58) Field of Classification Search ............... 606/34, 606/37, 39–42
See application file for complete search history.

(56) References Cited

U.S. PATENT DOCUMENTS

| | | |
|---|---|---|
| 2,031,682 A | 2/1936 | Frederick et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |

(Continued)

FOREIGN PATENT DOCUMENTS

DE  24 29 021 A1  1/1976

(Continued)

OTHER PUBLICATIONS

International Search Report from PCT/US03/37111; Jul. 21, 2004.

(Continued)

*Primary Examiner*—Linda C Dvorak
*Assistant Examiner*—Samuel Candler (57) ABSTRACT

A system and apparatus for controlling operating room equipment during an electrosurgical procedure is disclosed. The system includes an electrosurgical generator, a controller in electrical communication with and configured to control the electrosurgical generator and at least one operating room device, and a handpiece having a housing and a cable extending proximally from the housing providing electrical connection to the controller, the handpiece further includes first controls for controlling the generator and second controls for controlling at least one operating room device.

10 Claims, 4 Drawing Sheets

U.S. PATENT DOCUMENTS

| | | |
|---|---|---|
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,805,404 A * | 2/1989 | Dupin .................. 60/409 |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A | 7/1991 | Rydell |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A * | 2/1992 | Delahuerga et al. ........... 606/42 |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,190,541 A | 3/1993 | Abele et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A * | 6/1994 | Kuriloff et al. ................. 606/49 |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,366,464 A * | 11/1994 | Belknap .................... 606/159 |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |

| | | | | | | |
|---|---|---|---|---|---|---|
| 5,486,162 | A | 1/1996 | Brumbach | 6,074,386 | A | 6/2000 | Goble et al. |
| 5,496,314 | A | 3/1996 | Eggers | 6,074,387 | A | 6/2000 | Heim et al. |
| 5,498,654 | A | 3/1996 | Shimasaki et al. | 6,086,544 | A | 7/2000 | Hibner et al. |
| D370,731 | S | 6/1996 | Corace et al. | 6,090,123 | A | 7/2000 | Culp et al. |
| 5,531,722 | A | 7/1996 | Van Hale | 6,099,525 | A | 8/2000 | Cosmescu |
| 5,549,604 | A | 8/1996 | Sutcu et al. | 6,117,134 | A | 9/2000 | Cunningham et al. |
| 5,561,278 | A | 10/1996 | Rutten | 6,139,547 | A | 10/2000 | Lontine et al. |
| 5,599,346 | A | 2/1997 | Edwards et al. | D433,752 | S | 11/2000 | Saravia |
| 5,601,224 | A | 2/1997 | Bishop et al. | 6,142,995 | A | 11/2000 | Cosmescu |
| 5,609,573 | A | 3/1997 | Sandock | 6,146,353 | A | 11/2000 | Platt, Jr. |
| 5,626,575 | A | 5/1997 | Crenner | 6,149,648 | A | 11/2000 | Cosmescu |
| 5,630,417 | A | 5/1997 | Petersen et al. | 6,156,035 | A | 12/2000 | Songer |
| 5,630,426 | A | 5/1997 | Eggers et al. | 6,197,024 | B1 | 3/2001 | Sullivan |
| 5,630,812 | A | 5/1997 | Ellman et al. | 6,200,311 | B1 | 3/2001 | Danek et al. |
| 5,633,578 | A | 5/1997 | Eggers et al. | D441,077 | S | 4/2001 | Garito et al. |
| 5,634,912 | A | 6/1997 | Injev | 6,213,999 | B1 | 4/2001 | Platt, Jr. et al. |
| 5,634,935 | A | 6/1997 | Taheri | 6,214,003 | B1 | 4/2001 | Morgan et al. |
| 5,643,256 | A | 7/1997 | Urueta | 6,238,388 | B1 | 5/2001 | Ellman et al. |
| D384,148 | S | 9/1997 | Monson | 6,241,723 | B1 | 6/2001 | Heim et al. |
| 5,669,907 | A | 9/1997 | Platt, Jr. et al. | 6,241,753 | B1 | 6/2001 | Knowlton |
| 5,674,219 | A | 10/1997 | Monson et al. | 6,249,706 | B1 * | 6/2001 | Sobota et al. ............... 607/115 |
| 5,693,044 | A | 12/1997 | Cosmescu | 6,251,110 | B1 | 6/2001 | Wampler |
| 5,693,050 | A | 12/1997 | Speiser | 6,257,241 | B1 | 7/2001 | Wampler |
| 5,693,052 | A | 12/1997 | Weaver | 6,258,088 | B1 | 7/2001 | Tzonev et al. |
| 5,697,926 | A | 12/1997 | Weaver | 6,273,862 | B1 | 8/2001 | Privitera et al. |
| 5,702,360 | A | 12/1997 | Dieras et al. | 6,277,083 | B1 | 8/2001 | Eggers et al. |
| 5,702,387 | A | 12/1997 | Arts et al. | 6,286,512 | B1 | 9/2001 | Loeb et al. |
| 5,712,543 | A | 1/1998 | Sjostrom | 6,287,305 | B1 | 9/2001 | Heim et al. |
| 5,713,895 | A | 2/1998 | Lontine et al. | 6,287,344 | B1 | 9/2001 | Wampler et al. |
| 5,720,745 | A | 2/1998 | Farin et al. | 6,312,441 | B1 | 11/2001 | Deng |
| D393,067 | S | 3/1998 | Geary et al. | 6,325,799 | B1 | 12/2001 | Goble |
| 5,749,869 | A | 5/1998 | Lindenmeier et al. | D453,222 | S | 1/2002 | Garito et al. |
| 5,765,418 | A | 6/1998 | Rosenberg | D453,833 | S | 2/2002 | Hess |
| 5,776,092 | A | 7/1998 | Farin et al. | 6,350,276 | B1 | 2/2002 | Knowlton |
| 5,788,688 | A * | 8/1998 | Bauer et al. .................... 606/1 | 6,352,544 | B1 | 3/2002 | Spitz |
| 5,797,907 | A | 8/1998 | Clement | 6,355,034 | B2 | 3/2002 | Cosmescu |
| 5,800,431 | A | 9/1998 | Brown | 6,358,281 | B1 | 3/2002 | Berrang et al. |
| 5,836,897 | A | 11/1998 | Sakurai et al. | 6,361,532 | B1 | 3/2002 | Burek |
| 5,836,909 | A | 11/1998 | Cosmescu | D457,955 | S | 5/2002 | Bilitz |
| 5,836,944 | A | 11/1998 | Cosmescu | 6,386,032 | B1 | 5/2002 | Lemkin et al. |
| D402,030 | S | 12/1998 | Roberts et al. | 6,395,001 | B1 | 5/2002 | Ellman et al. |
| D402,031 | S | 12/1998 | Roberts et al. | 6,402,742 | B1 | 6/2002 | Blewett et al. |
| 5,843,109 | A | 12/1998 | Mehta et al. | 6,402,743 | B1 | 6/2002 | Orszulak et al. |
| 5,846,236 | A | 12/1998 | Lindenmeier et al. | 6,402,748 | B1 | 6/2002 | Schoenman et al. |
| 5,859,527 | A | 1/1999 | Cook | 6,409,725 | B1 | 6/2002 | Khandkar et al. |
| 5,868,768 | A | 2/1999 | Wicherski et al. | 6,413,255 | B1 | 7/2002 | Stern |
| 5,876,400 | A | 3/1999 | Songer | 6,416,491 | B1 | 7/2002 | Edwards et al. |
| 5,879,347 | A | 3/1999 | Saadat | 6,416,509 | B1 | 7/2002 | Goble et al. |
| 5,888,200 | A | 3/1999 | Walen | 6,425,912 | B1 | 7/2002 | Knowlton |
| 5,893,848 | A | 4/1999 | Negus et al. | 6,458,122 | B1 | 10/2002 | Pozzato |
| 5,893,849 | A | 4/1999 | Weaver | 6,458,125 | B1 | 10/2002 | Cosmescu |
| 5,893,862 | A | 4/1999 | Pratt et al. | 6,461,352 | B2 | 10/2002 | Morgan et al. |
| 5,913,864 | A | 6/1999 | Garito et al. | 6,464,702 | B2 | 10/2002 | Schulze et al. |
| 5,919,219 | A | 7/1999 | Knowlton | 6,471,659 | B2 | 10/2002 | Eggers et al. |
| 5,928,159 | A | 7/1999 | Eggers et al. | 6,494,882 | B1 | 12/2002 | Lebouitz et al. |
| 5,938,589 | A | 8/1999 | Wako et al. | 6,500,169 | B1 | 12/2002 | Deng |
| 5,941,887 | A | 8/1999 | Steen et al. | 6,511,479 | B2 | 1/2003 | Gentelia et al. |
| 5,944,737 | A | 8/1999 | Tsonton et al. | 6,526,320 | B2 | 2/2003 | Mitchell |
| 5,951,548 | A | 9/1999 | DeSisto et al. | 6,551,313 | B1 | 4/2003 | Levin |
| 5,951,581 | A | 9/1999 | Saadat et al. | 6,558,383 | B2 | 5/2003 | Cunningham et al. |
| 5,954,686 | A | 9/1999 | Garito et al. | 6,585,664 | B2 | 7/2003 | Burdorff et al. |
| 5,972,007 | A | 10/1999 | Sheffield et al. | 6,589,239 | B2 | 7/2003 | Khandkar et al. |
| 6,004,318 | A | 12/1999 | Garito et al. | 6,610,054 | B1 | 8/2003 | Edwards et al. |
| 6,004,333 | A | 12/1999 | Sheffield et al. | 6,610,057 | B1 | 8/2003 | Ellman et al. |
| 6,004,335 | A | 12/1999 | Vaitekunas et al. | 6,616,658 | B2 | 9/2003 | Ineson |
| 6,010,499 | A | 1/2000 | Cobb | 6,618,626 | B2 | 9/2003 | West, Jr. et al. |
| 6,022,347 | A | 2/2000 | Lindenmeier et al. | 6,620,161 | B2 | 9/2003 | Schulze et al. |
| 6,045,564 | A | 4/2000 | Walen | 6,632,193 | B1 | 10/2003 | Davison et al. |
| 6,063,050 | A | 5/2000 | Manna et al. | 6,652,514 | B2 | 11/2003 | Ellman et al. |
| 6,068,603 | A | 5/2000 | Suzuki | 6,662,053 | B2 | 12/2003 | Borkan |
| 6,068,627 | A | 5/2000 | Orszulak et al. | 6,669,691 | B1 | 12/2003 | Taimisto |
| 6,070,444 | A | 6/2000 | Lontine et al. | 6,685,701 | B2 | 2/2004 | Orszulak et al. |
| 6,071,281 | A | 6/2000 | Burnside et al. | 6,685,704 | B2 | 2/2004 | Greep |

| | | |
|---|---|---|
| 6,689,146 B1 * | 2/2004 | Himes .................. 606/167 |
| 6,702,812 B2 | 3/2004 | Cosmescu |
| 6,710,546 B2 * | 3/2004 | Crenshaw ................ 315/86 |
| 6,712,813 B2 | 3/2004 | Ellman et al. |
| 6,719,746 B2 * | 4/2004 | Blanco .................. 604/506 |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B1 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 6,994,707 B2 * | 2/2006 | Ellman et al. ............. 606/42 |
| 7,033,353 B2 | 4/2006 | Stoddard et al. |
| D521,641 S | 5/2006 | Reschke et al. |
| D535,396 S | 1/2007 | Reschke et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 * | 4/2003 | Borders et al. ............. 5/600 |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 * | 2/2004 | Yamaki et al. ............. 607/60 |
| 2004/0034346 A1 | 2/2004 | Stern et al. |
| 2004/0054370 A1 | 3/2004 | Given |
| 2004/0092927 A1 | 5/2004 | Podhajsky et al. |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0138920 A1 * | 7/2004 | Sawanaga et al. ............ 705/2 |
| 2004/0143677 A1 * | 7/2004 | Novak .................. 709/238 |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 * | 9/2004 | Wang et al. ................ 606/1 |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0230262 A1 | 11/2004 | Sartor et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0107782 A1 | 5/2005 | Reschke |
| 2005/0113817 A1 | 5/2005 | Isaacson et al. |
| 2005/0113818 A1 | 5/2005 | Sartor et al. |
| 2005/0113823 A1 | 5/2005 | Reschke et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0178667 A1 | 8/2006 | Sartor et al. |
| 2007/0049926 A1 | 3/2007 | Sartor |
| 2007/0093810 A1 | 4/2007 | Sartor |

FOREIGN PATENT DOCUMENTS

| | | |
|---|---|---|
| DE | 24 60 481 A1 | 6/1976 |
| DE | 30 45 996 | 7/1982 |
| EP | 0 186 369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1645234 | 4/2006 |
| EP | 1656900 | 5/2006 |
| EP | 1852078 | 11/2007 |
| FR | 2235669 | 1/1975 |
| FR | 2798579 | 3/2001 |
| WO | WO94/20032 | 9/1994 |
| WO | WO 96/39086 | 12/1996 |

| WO | WO 98/43264 | 10/1998 |
| WO | WO01/64122 | 9/2001 |
| WO | WO 02/47568 A1 | 6/2002 |
| WO | WO 2004/010883 A1 | 2/2004 |
| WO | WO 2004/045436 | 6/2004 |
| WO | WO 2004/073753 A2 | 9/2004 |
| WO | WO 2005/060849 A1 | 7/2005 |

OTHER PUBLICATIONS

International Search Report from PCT/US04/04685; Aug. 6, 2004.
International Search Report from EP/0401/5980; Sep. 30, 2004.
International Search Report from PCT/US03/22900; Nov. 20, 2003.
European Search Report from Application EP 07009028 dated Jul. 16, 2007.
International Search Report EP 06 005 540.7 dated Sep. 24, 2007.
International Search Report from EP 06 01 4461 dated Oct. 31, 2006.
ISR from EP 05019882.9 dated Feb. 16, 2006.
ISR from EP 05021777.7 dated Feb. 23, 2006.
International Search Report from European Application No. EP 08 00 2357 dated Jun. 30, 2008.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).

* cited by examiner

HANDHELD ELECTROSURGICAL APPARATUS FOR CONTROLLING OPERATING ROOM EQUIPMENT

BACKGROUND

1. Technical Field

The present disclosure relates generally to electrosurgical instruments and, more particularly, to an electrosurgical handpiece having a plurality of hand-accessible variable controls.

2. Background of Related Art

During electrosurgery, a source or active electrode delivers energy, such as radio frequency (RF) energy, from an electrosurgical generator to a patient and a return electrode or a plurality thereof carry current back to the electrosurgical generator. In monopolar electrosurgery, the source electrode is typically a hand-held instrument placed by the surgeon at the surgical site and the high current density flow at this electrode creates the desired surgical effect of ablating, cutting or coagulating tissue. The patient return electrodes are placed at a remote site from the source electrode and are typically in the form of pads adhesively adhered to the patient.

Bipolar electrosurgery is conventionally practiced using an electrosurgical forceps-type device, where the active and return electrodes are housed within opposing forceps' jaws. The return electrode is placed in close proximity to the active electrode (current supplying) such that an electrical circuit is formed between the two electrodes (e.g., electrosurgical forceps). In this manner, the applied electrical current is limited to the body tissue positioned between the electrodes.

Electrosurgical instruments have become widely used by surgeons in recent years. Accordingly, a need has developed for equipment and instruments which are easy to handle, are reliable and are safe in an operating environment. Generally, most electrosurgical instruments are hand-held instruments, e.g., an electrosurgical pencil, which transfer radio-frequency (RF) electrical energy to a tissue site.

Electrosurgical procedures are performed in operating rooms including a variety of equipment, e.g., an operating table, operating lights, smoke evacuation systems, insufflation systems, etc. During surgical procedures, the surgeon and his staff need to operate each of these devices. However, controls for these devices are located throughout the operating room away from the sterile field instead of a single central location therein. In order to interact with the controls, the surgeon must momentarily stop the procedure and focus his attention away from the sterile field. For instance, to adjust the light output level the surgeon must move outside the sterile field to lighting controls or ask for assistance to do so. These methods have a few drawbacks, for example, asking another person to adjust the controls does not provide the same level of exactitude and feedback that the surgeon would be able to achieve in adjusting the desired apparatus himself. Furthermore, the adjustment accomplished by the surgeon himself requires that he leave the sterile field and cease the procedure temporarily, resulting in unneeded interruptions and risks of contamination of the surgical site.

Therefore, there is a need for a control system having controls for a variety of operating room equipment disposed on a single apparatus found within the sterile field.

SUMMARY

The present disclosure provides for an apparatus which includes controls for a variety of operating room devices therein. The apparatus is held by a surgeon during surgical procedures within the sterile field providing the surgeon immediate control of the operating room devices, such as overhead lighting, insufflation unit, operating table, and the like. The apparatus is connected to a central controller which in turn is connected to the operating room devices. The apparatus may be a stand-alone device or be incorporated in a variety of surgical devices, such as irrigation apparatuses and electrosurgical pencils.

According to one embodiment of the present disclosure, a system for controlling operating room equipment during an electrosurgical procedure is disclosed. The system includes an electrosurgical generator, a controller in electrical communication with and configured to control the electrosurgical generator and at least one operating room device, and a handpiece having a housing and a cable extending proximally from the housing providing electrical connection to the controller, the handpiece further includes first controls for controlling the generator and second controls for controlling at least one operating room device.

According to another embodiment of the present disclosure, an apparatus for controlling operating room equipment during an electrosurgical procedure is disclosed. The apparatus includes a housing, a cable extending proximally from the housing providing electrical connection to a controller, the controller in electrical communication with and configured to control an electrosurgical generator and at least one operating room device, first controls for controlling the generator, and second controls for controlling at least one operating room device.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Preferred embodiments of the present disclosure will be described herein below with reference to the accompanying drawings. In the following description, well-known functions or constructions are not described in detail to avoid obscuring the present disclosure in unnecessary detail. As used herein, the term "distal" refers to that portion which is further from the user while the term "proximal" refers to that portion which is closer to the user or surgeon.

Figure 1:
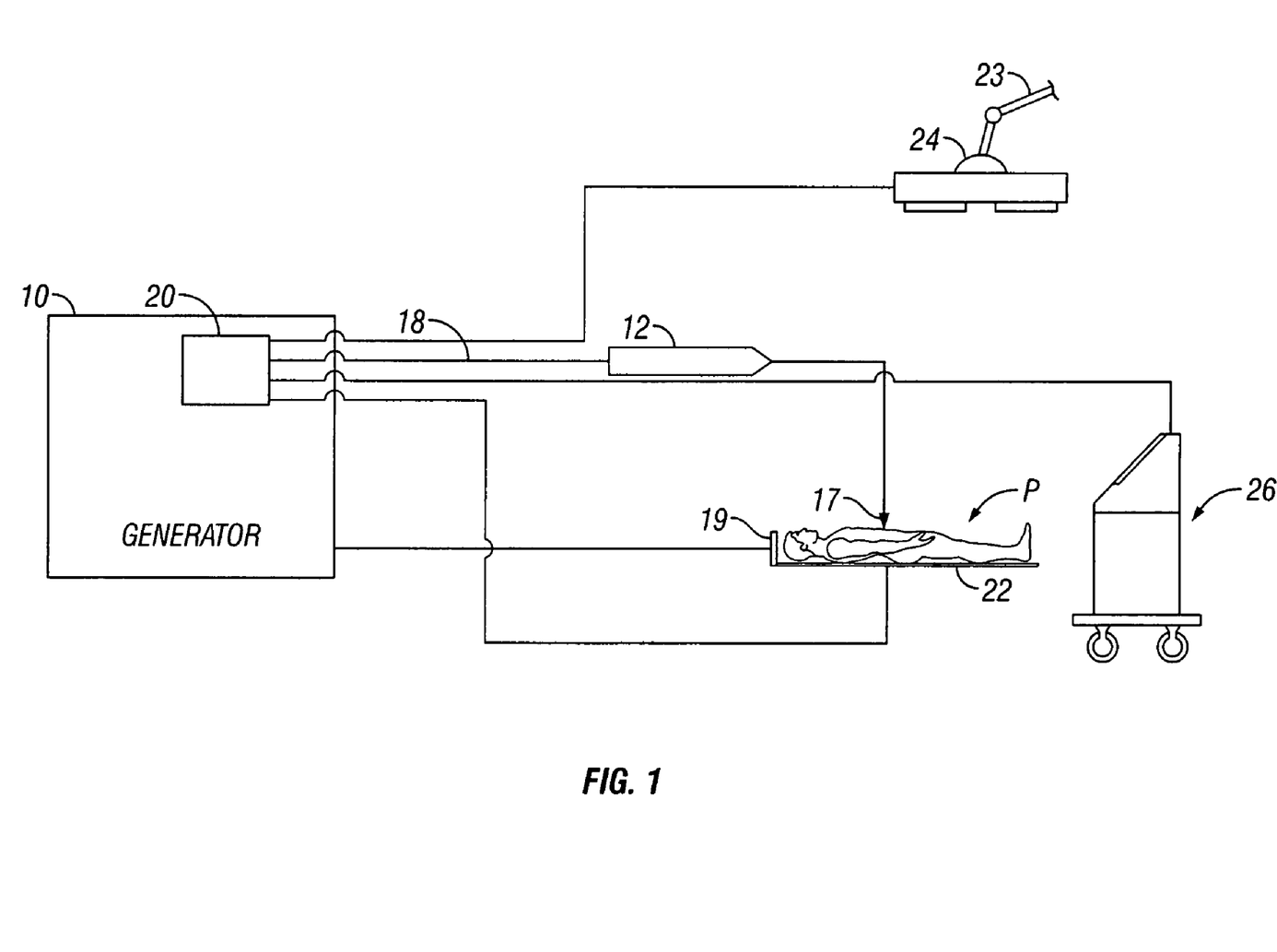
FIG. 1 is a block diagram illustrating in general an electrosurgical system including a handpiece according to the present disclosure.

FIG. 1 shows an electrosurgical system including a generator 10 and a handpiece 12 (e.g., an electrosurgical pencil) having an active electrode 17 at a distal end thereof which is brought in contact with a patient P to effect a cut and/or coagulation procedure depending upon the operating mode selected. The active electrode 17 is an electrically conducting element which is usually elongated and may be in the form of a thin flat blade with a pointed or rounded distal end. Alternatively, the active electrode 17 may include an elongated narrow cylindrical needle which is solid or hollow with a flat, rounded, pointed or slanted distal end.

Attached to the patent P is a return electrode 19 which returns the electrosurgical current from the patient P to the generator 10. The handpiece 12 is connected to the generator 10 via a cable 18 extending from a proximal end of the handpiece 12. The cable 18 includes electrical wires for supplying the electrosurgical power to the active electrode 17 as well as electrical power for the controls of the handpiece 12.

The active electrode 17 may be used laparoscopically, e.g., inserted into a body cavity through a percutaneous incision. To accomplish this, the electrode 17 may be introduced into a body cavity through a conventional trocar (not shown). The trocar may include an elongated tube which penetrates the body cavity with its distal end and the electrode 17 is introduced thereto through its proximal end. In addition, the trocar may include a hemostatic valve disposed at its proximal end to prevent backflow of fluids.

The handpiece 12 may also include an irrigation tube (not shown) which irrigates the surgical site. Other components of the irrigation system (e.g., irrigation fluid supply, valve mechanisms, etc.) may be disposed within the generator 10 or within a separate stand-alone device (e.g., a cassette). The irrigation and suction lines are connected from the irrigation system to the handpiece 12 and thereafter to the irrigation tube and may be included within the cable 18.

Other surgical equipment may also be used in conjunction with electrosurgical equipment, such as an operating table 22, operating room lighting 24, and an insufflation unit 26. The operating table 22 may include a plurality of servo actuators which activate component pieces of the operating table 22 (e.g., head section, middle section, leg section, etc.). In particular, servo actuators may tilt and/or rotate the sections of the operating table 22 to position the patient P in a desired posture.

The lighting 24 may be any operating room lighting fixture for illuminating the surgical site. The lighting 24 is positioned above the operating table 22 and includes a support arm 23. The lighting 24 includes controls for turning the lighting 24 on and off, adjusting intensity of the light. In addition, the lighting 24 may include servo actuators which modify the position thereof by adjusting the support arm 23.

The insufflation unit 26 inflates body cavities, which is a conventional procedure used during laparoscopic surgery. Insufflation is accomplished by pumping gas into body cavities to provide more space for the surgeon to maneuver various laproscopic instruments. The insufflation unit 26 may include controls for adjusting insufflation pressure, turning on ventilation of insufflation gas to clear smoke generated during laparoscopic electrosurgical procedures, etc.

Conventionally, controls for the operating room equipment are disposed on the equipment itself. According to the present disclosure, the controls for the operating table 22, the lighting 24, and the insufflation unit 26 are located at the handpiece 12. This allows the surgeon to control a multitude of operating room devices within the sterile field and alleviates the problems associated with conventional control schemes of operating room equipment. The central controls may be incorporated in a control device held by the surgeon within the sterile field. In addition, the controls may be included on any instruments used by the surgeon during operating procedures. In particular, the controls may be disposed on the handpiece 12. This allows the surgeon to control the operating parameters of the generator 10 as well as other operating equipment (e.g., the operating table 22, the lighting 24, and the insufflation unit 26). The handpiece 12 includes controls which transmit control signals to a central controller 20 which then controls each of the operating room devices. The central controller 20 may be a stand-alone device or be incorporated into the circuitry and/or housing of the generator 10. The controller 20 includes inputs for accepting control signals from the handpiece 12 and outputs for interfacing with a variety of operating room equipment (e.g., the generator 20, etc.). In addition, the controller 20 may include other electronic, electrical, or electromechanical components (e.g., relays) to accept inputs from the handpiece 12 and transmit them to the operating room equipment.

Figure 2:
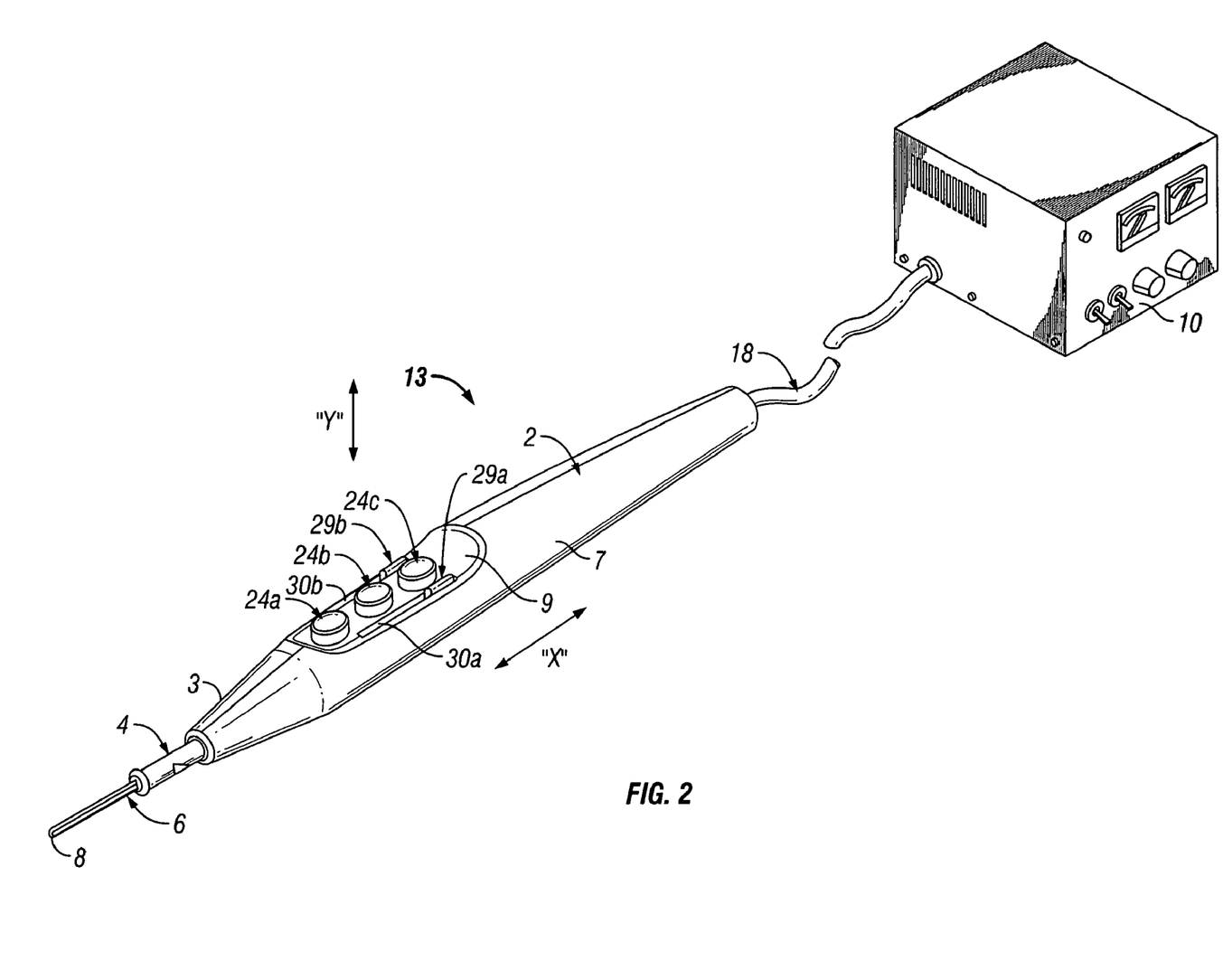
FIG. 2 is a perspective view of an electrosurgical pencil according to the present disclosure.

The handpiece 12 may be in a shape of an electrosurgical pencil. Typically, the electrosurgical pencil may be operated by a handswitch or a footswitch. FIG. 2 shows a perspective view of an electrosurgical pencil constructed in accordance with one embodiment of the present disclosure and generally referenced by numeral 13. While the following description will be directed towards electrosurgical pencils, it is envisioned that the features and concepts (or portions thereof) of the present disclosure can be applied to any electrosurgical type instrument, e.g., forceps, suction coagulator, vessel sealers, etc.

Figure 3:
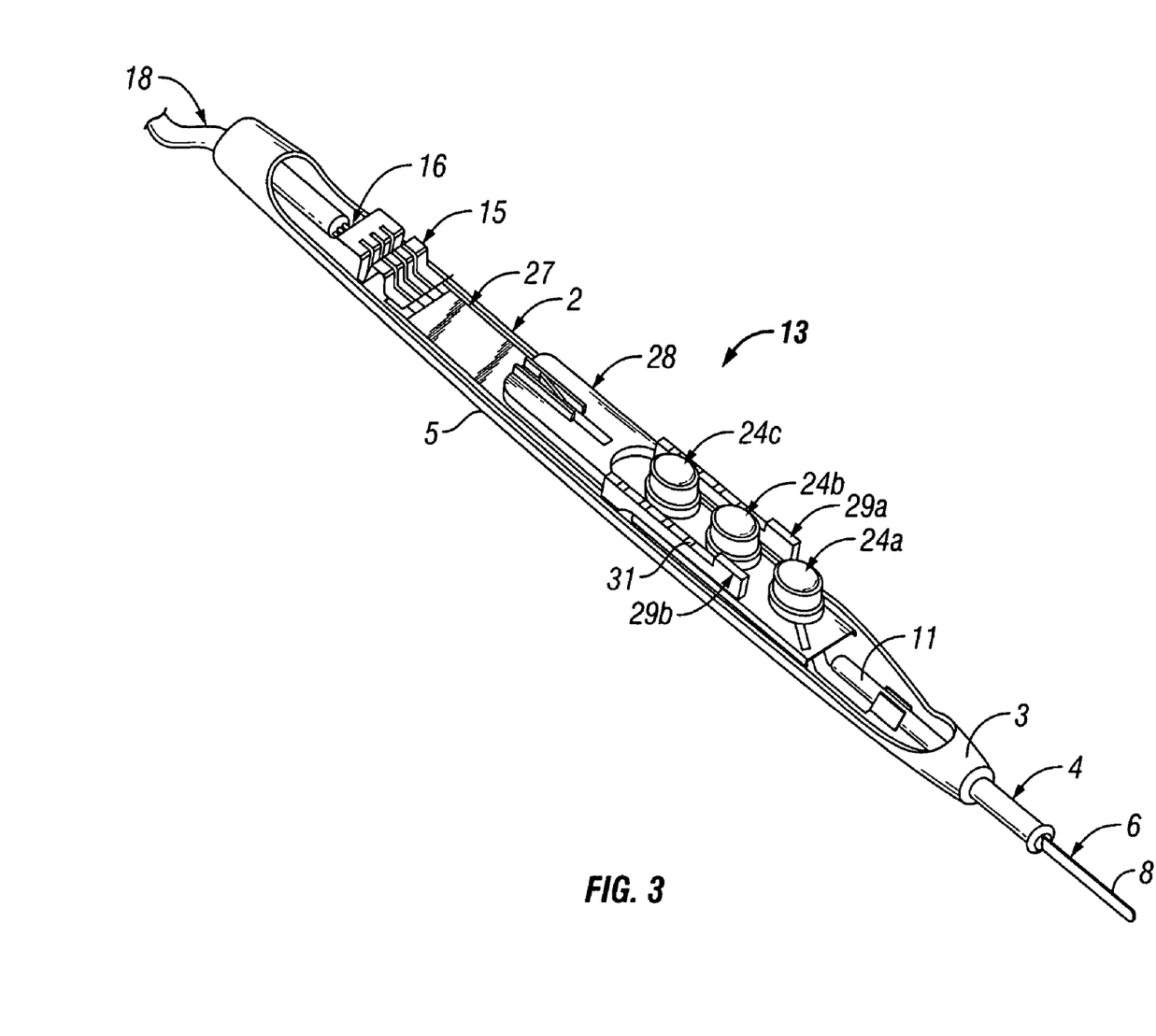
FIG. 3 is a partially broken away perspective view of the electrosurgical pencil of FIG. 2.
Figure 4:
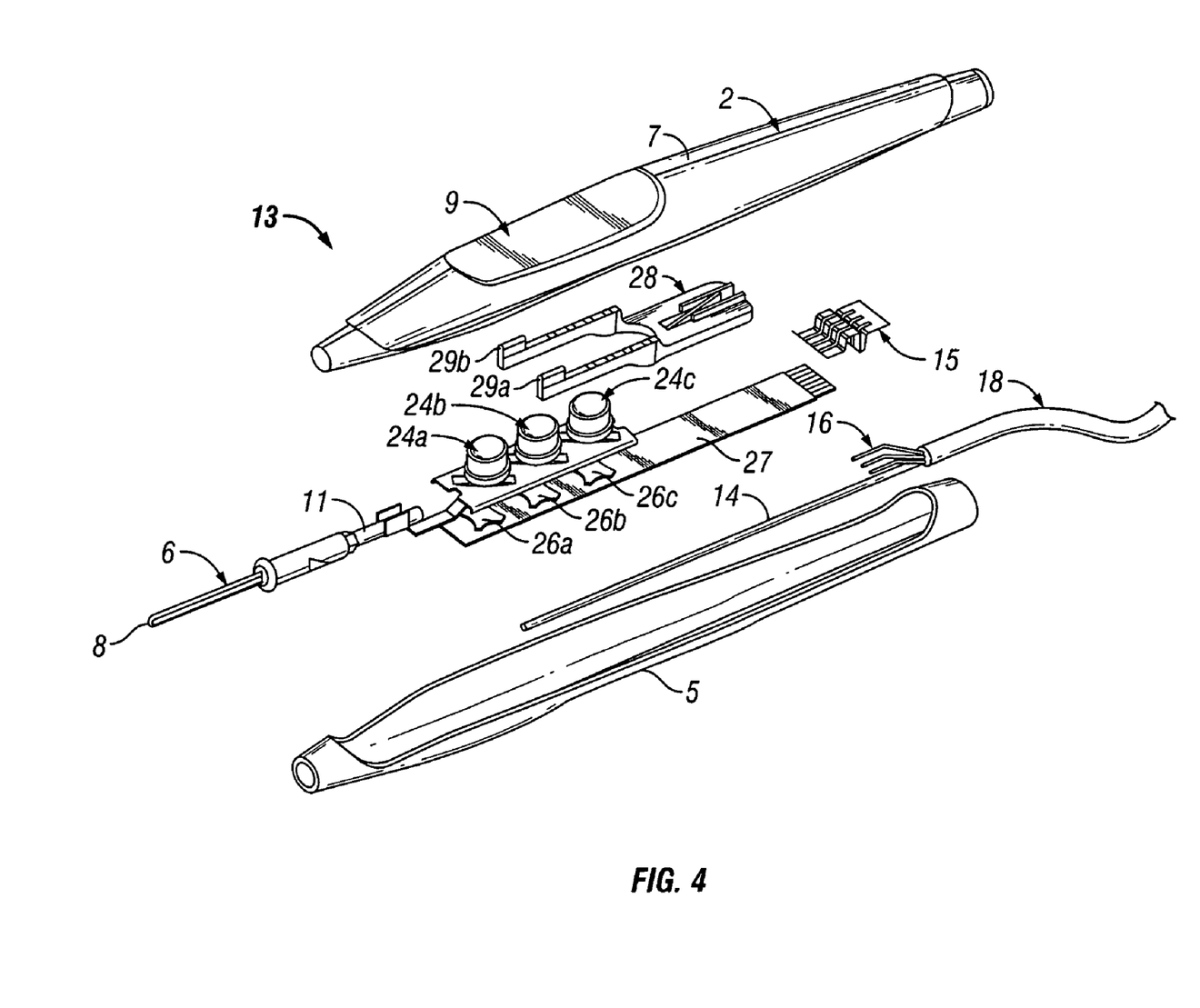
FIG. 4 is an exploded perspective view of the electrosurgical pencil of FIG. 2.

As shown in FIGS. 2-4, electrosurgical pencil 13 includes an elongated housing 2 configured and adapted to support a blade receptacle 4 at a distal end 3 thereof which, in turn, receives a replaceable electrocautery end effector 6 (e.g., the active electrode 17) in the form of a loop and/or blade therein. Electrocautery blade 6 is understood to include a planar blade, a loop, a needle and the like. A distal end portion 8 of blade 6 extends distally from receptacle 4 while a proximal end portion 11 (see FIG. 3) of blade 6 is retained within distal end 3 of housing 2. It is contemplated that electrocautery blade 6 is fabricated from a conductive type material, such as, for example, stainless steel, or is coated with an electrically conductive material.

As shown, electrosurgical pencil 13 is coupled to a conventional electrosurgical generator 10 via a cable 18, which includes a transmission wire 14 (see FIG. 4) which electrically interconnects electrosurgical generator 10 with proximal end portion 11 of electrocautery blade 6. Cable 18 further includes control wires 16 which electrically interconnect switches (as will be described in greater detail below), supported on an outer surface 7 of housing 2, with electrosurgical generator 10. For the purposes herein the terms "switch" or "switches" includes electrical actuators, mechanical actuators, electro-mechanical actuators (rotatable actuators, pivotable actuators, toggle-like actuators, buttons, etc.) or optical actuators.

Turning back to FIGS. 2-4, as mentioned above, electrosurgical pencil 13 further includes at least one activation switch, preferably three activation switches 24a-24c, each of which are supported on an outer surface 7 of housing 2. The activation switch 24a activates the insufflation unit 26 and initiates the inflation process. The activation switch 24b activates the siphoning process of the insufflation unit 26. The activation switch 24c is configured to turn on or off the lighting 24. Those skilled in the art will appreciate that the pencil 13 may include additional activation switches for adjusting a variety of functions of the operating room equipment.

Each activation switch 24a-24c is operatively connected to a location on a tactile element 26a-26c (e.g., a snap-dome is shown) which, in turn, controls various operating room equipment. More particularly, tactile elements 26a-26c are operatively connected to a voltage divider network 27 (hereinafter "VDN 27") which forms a switch closure (e.g., here shown as a film-type potentiometer). For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage.

In use, depending on which activation switch 24a-24c is depressed a respective switch 26a-26c is pressed into contact with VDN 27 and a characteristic signal is transmitted to the controller 20 via control wires 16, which then transmits signals to corresponding operating room equipment. Control voltage is supplied to the electrosurgical pencil 13 by a secondary power source (not shown) (e.g., a battery). The secondary power source along with the controls of the electrosurgical pencil 13 (e.g., activation switch 24a-24c) and the controller 20 form a control loop. Control wires 16 are preferably electrically connected to switches 26a-26c via a terminal 15 (see FIGS. 3 and 4). The controller 20 includes a circuit for interpreting and responding to the VDN settings.

In operation and depending on the particular desired operation of one of the operating room equipment, the surgeon depresses one of activation switches 24a-24c, in the direction indicated by arrow "Y" (see FIG. 1) thereby urging a corresponding switch 26a-26c against VDN 27 and thereby transmitting a respective characteristic signal to electrosurgical controller 20.

Those skilled in the art will appreciate that the pencil 13 also includes activation switches configured and adapted to control the mode and/or "waveform duty cycle" to achieve a desired surgical intent (not shown). Typically, the "modes" relate to the various electrical waveforms, e.g., a cutting waveform has a tendency to cut tissue, a coagulating wave form has a tendency to coagulate tissue and a blend wave form is somewhere between a cut and coagulate wave from. The power or energy parameters are typically controlled from outside the sterile field which requires an intermediary like a circulating nurse to make such adjustment. A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. The hemostatic effect/function can be defined as having waveforms with a duty cycle from about 1% to about 12%. The blending effect/function can be defined as having waveforms with a duty cycle from about 12% to about 75%. The cutting and/or dissecting effect/function can be defined as having waveforms with a duty cycle from about 75% to about 100%. It is important to note that these percentages are approximated and may be customized to deliver the desired surgical effect for various tissue types and characteristics.

Electrosurgical pencil 13 further includes an intensity controller (not shown) for adjusting the intensity of the electrosurgical current. The intensity controller may be in the form of a sliding controller as discussed in detail below. The electrosurgical pencil 13 includes a sliding controller 28 having a pair of nubs 29a, 29b which are slidingly supported, one each, in respective guide channels 30a, 30b, formed in outer surface 7 of housing 2 on either side of activations switches 24a-24c. The nub 29a is configured to control the tilt of the operating table 22, sliding the nub 29a along the direction indicated by double-headed arrow "X" toward the distal end of the pencil 13 tilts the table 22 forward, while sliding the nub 29a toward the proximal end tilts the table 22 backward. Tilting of the operating table 22 allows for adjustment of an angle at which the torso of the patient P is positioned to create clearances between organs and abdominal wall for insertion of endoscopic instruments. It is envisioned that activation switches may be used instead of sliding nubs to control tilting of the operating table 22, where each of the activation switches tilt the table 22 in a corresponding direction.

The nub 29b is configured to control the intensity of the lighting 24, whereas sliding the nub 29b along the direction indicated by double-headed arrow "X" toward the proximal end of the pencil 13 decreases the intensity of the light and sliding the nub 29a toward the distal end increases the intensity. Those skilled in the art will understand that the pencil 13 may include additional controls for controlling other functions of the lighting 24 such as lateral, longitudinal, and vertical position of the lighting 24, if corresponding position adjusters are included (e.g., servo actuators, hydraulics, etc.).

Preferably, sliding controller 28 is a slide potentiometer wherein nubs 29a, 29b have a first position (e.g., proximal-most position closest to cable 18) corresponding to a relative low intensity setting, a second position (e.g., a distal-most position closest to electrocautery end effector 6) corresponding to a relative high intensity setting, and a plurality of intermediate positions corresponding to intermediate intensity settings. As can be appreciated, the intensity settings from proximal end to distal end may be reversed as well, e.g., high to low. It is contemplated that nubs 29a, 29b of sliding controller 28 and corresponding guide channels 30a, 30b may be provided with a series of cooperating discrete or dented positions defining a series of discrete values, preferably five, to allow easy selection of the output intensity from the low intensity setting to the high intensity setting. The series of cooperating discrete or detented positions also provide the surgeon with a degree of tactile feedback. As best seen in FIG. 3, sliding controller 28 can include a series of indicia 31 provided thereon which are visible through guide channels 30a, 30b. Indicia 31 are preferably a series of numbers (e.g., numbers 1-5) which reflect the level of intensity that is to be transmitted. Alternatively, level indicators may be printed alongside the sides of guide channels 30a, 30b along which nubs 29a, 29b slide.

It is envisioned that the sliding controller 28 may be replaced by a current divider network (e.g., a rheostat) wherein, the rheostat has a first position corresponding to one setting, a second position corresponding to another intensity and a plurality of other positions corresponding to settings between the minimum and the maximum settings. For instance, in reference to the controls for the lighting 24, the minimum setting would dim the lights while the maximum setting adjusts the lights for maximum illumination, with other settings representing medium light intensity.

By providing nubs 29a, 29b on either side of activation switches 24a-24c, controller 28 can be easily manipulated by either hand of the user or the same electrosurgical pencil can be operated by a right-handed or a left-handed user. An example of an electrosurgical pencil for controlling the modes and intensity is disclosed in a commonly-owned U.S. patent application Ser. No. 10/718,113 entitled "Electrosurgical Pencil with Improved Controls" which is hereby incorporated by reference in its entirety herein.

It is also contemplated that sliding controller 28 can be configured and adapted to provide a degree of tactile feedback. Alternatively, audible feedback can be produced from sliding controller 28 (e.g., a "click"), from the generator 10 (e.g., a "tone") and/or from an auxiliary sound-producing device such as a buzzer (not shown).

Preferably, as seen in FIGS. 2 and 4, sliding controller 28 and activation switches 24a-24c are supported in a recess 9 formed in outer wall 7 of housing 2. Desirably, activation switches 24a-24c are positioned at a location where the fingers of the surgeon would normally rest when electrosurgical pencil 13 is held in the hand of the surgeon while nubs 29a, 29b of sliding controller 28 are placed at locations which would not be confused with activation switches 24a-24c. Alternatively, nubs 29a, 29b of sliding controller 28 are positioned at locations where the fingers of the surgeon would normally rest when electrosurgical pencil 13 is held in the hand of the surgeon while activation switches 24a-24c are placed at locations which would not be confused with nubs 29a, 29b of sliding controller 28. In addition, recess 9 formed in outer wall 7 of housing 2 advantageously minimizes inadvertent activation (e.g., depressing, sliding and/or manipulating) of activation switches 24a-24c and sliding controller 28 while in the surgical field and/or during the surgical procedure.

As seen in FIG. 4, electrosurgical pencil 13 includes a molded/contoured hand grip 5 which substantially surrounds the distal and proximal ends of housing 2 as well as the underside of housing 2. Contoured hand grip 5 is shaped and dimensioned to improve the handling of electrosurgical pencil 13 by the surgeon. Accordingly, less pressure and gripping force is required to use and/or operate electrosurgical pencil 13 thereby potentially reducing the fatigue experienced by the surgeon.

Those skilled in the art will understand that the above-described embodiments of controls disposed on an electrosurgical pencil can incorporate controls for a variety of operating room equipment not discussed in detail, such as irrigation systems and the like. In addition, the skilled in the art will appreciate that the centralized controls of the present disclosure can be incorporated into a stand-alone apparatus configured to be held by the surgeon (e.g., attached to the electrosurgical pencil) during operating procedures or into existing surgical devices, such as irrigation devices and the like.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A system for controlling and effecting activation of operating room equipment disposed outside a sterile field during an electrosurgical procedure inside the sterile field, the system comprising:
    an electrosurgical generator configured to deliver energy to the sterile field and including a controller;
    the controller being in electrical communication with and configured to control the electrosurgical generator and at least one operating room device disposed outside the sterile field to produce an effect outside the sterile field; and
    a handpiece having a housing and a cable extending from the housing providing electrical connection to the controller, the handpiece further includes first controls for controlling the generator and second controls for controlling and effecting activation and adjustment of at least one operating room device disposed outside the sterile field to produce an effect outside the sterile field, including:
        activation and adjustment of an operating room bed;
        activation and adjustment of an operating room light source; and
        activation and adjustment of an insufflation device;
    wherein each of the first and second controls is in direct electrical communication with the controller, wherein the second controls include at least one sliding controller for activating and adjusting the at least one operating room device.

2. A system as in claim 1, wherein the first controls include at least one first activation switch supported on the housing, the at least one first switch being configured and adapted to selectively complete a control loop extending from the controller upon actuation thereof.

3. A system as in claim 1, wherein the second controls include at least one second activation switch supported on the housing, the at least one second switch being configured and adapted to selectively complete a control loop extending from the controller upon actuation thereof.

4. A system as in claim 1, wherein the first controls include at least one first voltage divider network supported on the housing, the at least one first voltage divider network being electrically connected to the controller.

5. A system as in claim 4, wherein the at least one first voltage divider network is a potentiometer.

6. A system as in claim 5, wherein the potentiometer has discrete values.

7. A system as in claim 1, wherein the second controls include at least one second voltage divider network supported on the housing, the at least one second voltage divider network being electrically connected to the controller.

8. A system as in claim 7, wherein the at least one second voltage divider network is a potentiometer.

9. A system as in claim 8, wherein the potentiometer has discrete values.

10. An apparatus as in claim 1, wherein the first controls include at least one sliding controller for adjusting the intensity of the energy of the electrosurgical generator.

* * * * *